United States Patent [19]

Kitahara

[11] Patent Number: 4,601,809
[45] Date of Patent: Jul. 22, 1986

[54] OXYGEN CONCENTRATION DETECTING SYSTEM USING OXYGEN SENSOR INCLUDING OXYGEN ION PUMP

[75] Inventor: Tsuyoshi Kitahara, Ina, Japan

[73] Assignee: Nissan Motor Co., Ltd., Yokohama, Japan

[21] Appl. No.: 723,298

[22] Filed: Apr. 15, 1985

[30] Foreign Application Priority Data

Apr. 16, 1984 [JP] Japan .................................. 59-75063

[51] Int. Cl.⁴ ............................................. G01N 27/56
[52] U.S. Cl. .................................. 204/406; 123/440; 123/489; 204/412; 204/425
[58] Field of Search ............... 204/401, 402, 406, 412, 204/424, 425, 426, 427; 123/489, 332, 333, 440; 73/1 G; 60/276

[56] References Cited

U.S. PATENT DOCUMENTS

| 4,075,988 | 2/1978 | Kato | 123/333 |
| 4,088,543 | 5/1978 | Roka | 204/428 X |
| 4,279,142 | 7/1981 | McIntyre | 73/1 G |
| 4,450,065 | 5/1984 | Yamada et al. | 204/426 X |
| 4,484,497 | 11/1984 | Hibino | 123/333 X |
| 4,498,968 | 2/1985 | Yamada et al. | 204/426 X |
| 4,505,806 | 3/1985 | Yamada | 204/427 X |
| 4,505,807 | 3/1985 | Yamada | 204/429 X |
| 4,532,013 | 7/1985 | Dietz et al. | 204/402 X |

FOREIGN PATENT DOCUMENTS

58-57050 5/1983 Japan.

Primary Examiner—John F. Niebling
Assistant Examiner—Nam X. Nguyen
Attorney, Agent, or Firm—Schwartz, Jeffery, Schwaab, Mack, Blumenthal & Evans

[57] ABSTRACT

A system for detecting the concentration of oxygen in a gas which comprises an oxygen sensor having a first solid electrolyte cell, which produces an electrical output representing a difference between oxygen partial pressures on the opposite two sides of a solid electrolyte layer, and a second solid electrolyte cell which acts as an oxygen ion pump by application of a current thereto and is used to control the oxygen partial pressure in a fraction of the gas admitted into the sensor. The current is controlled so as to render the output of the oxygen sensor equal to a target value. The system includes means for continuously making a judgement whether the gas under inspection is equivalent to the air or not. When the atmospheric condition of the gas is established the target value is varied so as to avoid undesirable increase in the current intensity. This is favorable for durability of the oxygen sensor. A provisional output signal representing the current intensity is corrected based on the output value obtained under the atmospheric condition. This system is suitable for use in detecting the air/fuel ratio in an internal combustion engine by detecting oxygen concentration in the exhaust gas.

19 Claims, 6 Drawing Figures

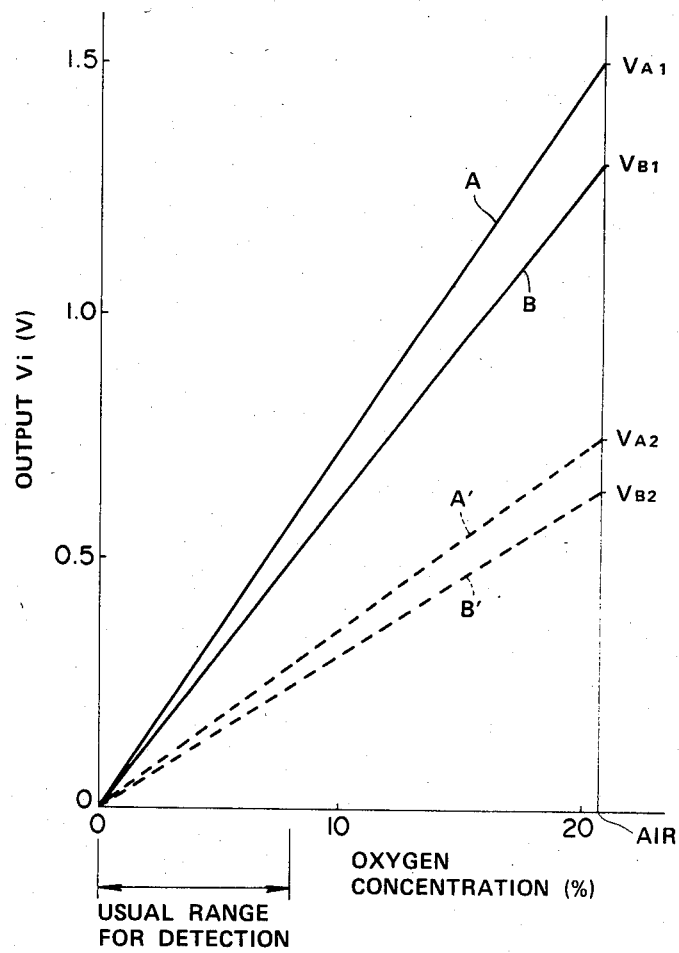

OXYGEN CONCENTRATION DETECTING SYSTEM USING OXYGEN SENSOR INCLUDING OXYGEN ION PUMP

BACKGROUND OF THE INVENTION

This invention relates to a system for detecting the concentration of oxygen in gases by using an oxygen sensor having a solid electrolyte cell which acts as an oxygen partial pressure detector and another solid electrolyte cell which acts as an oxygen ion pump by application of a current thereto. This system is suitable for use in detecting the air/fuel ratio in an internal combustion engine by detecting the concentration of oxygen in the exhaust gas.

For use in various combustion gases, oxygen sensors using an oxygen ion conductive solid electrolyte such as zirconia are well known. In the current automotive internal combustion engines, it is popular to perform feedback control of air/fuel ratio by using an oxygen sensor to estimate an actual air/fuel ratio by detecting the concentration or partial pressure of oxygen in the exhaust gas.

As is well known, an oxygen sensor for use in exhaust gases can be constructed by forming an electrode layer on an outer surface of a tubular body of zirconia or an alternative ceramic solid electrolyte and another electrode layer on the inner surface. The tubular body is closed at one end, and the outer side of this oxygen sensor is exposed to the exhaust gas while the inner side is exposed to a reference gas such as the atmospheric air. When the nominal air/fuel ratio in the engine is nearly stoichiometric, this sensor can be used in the manner of an oxygen concentration cell that generates an electromotive force between the two electrodes according to a difference between the partial pressures of oxygen on the outer and inner sides of the zirconia tube without need of applying any external voltage or current to the sensor. However, when the nominal air/fuel ratio is substantially higher than the stoichiometric ratio as in the cases of so-called lean-burn engines this oxygen sensor has to be used in a different manner. For example, it is known to apply a constant voltage across the outer and inner electrodes of the sensor to measure a current that is produced by the constant voltage and flows through the solid electrolyte. The current varies proportionally to the concentration of oxygen in the exhaust gas, and, insofar as the air/fuel ratio in the engine is not lower than the stoichiometric ratio, the oxygen concentration in the exhaust gas is nearly proportional to the air/fuel ratio.

In practice, however, there is a problem that the oxygen-sensitive characteristic of the sensor gradually changes during long exposure of the sensor to high temperature exhaust gases due to deposition of solid particles contained in the exhaust gases and/or repeated thermal shocks. Also it is a problem that industrially produced sensors of the same design are liable to be somewhat different from one another in the oxygen-sensitive characteristic. Therefore, some measures should be taken for avoidance of an increase in errors in the feedback control of air/fuel ratio by reason of these problems.

Japanese patent application primary publication No. 58-57050 (1983) relates to feedback control of air/fuel ratio in an automotive engine operated with a fuel-lean mixture and proposes to calibrate the oxygen-sensitive characteristic of the above described oxygen sensor, which is operated with application of a constant voltage thereto, by checking the level of the aforementioned current while the exhaust gas flowing along the outer side of the sensor is equivalent to the atmospheric air. According to the proposal, cutoff of fuel feed is detected in order to make a judgement that an atmospheric condition is realized in the exhaust system at the location of the oxygen sensor after the lapse of a predetermined length of time from the moment of the cutoff of fuel feed. At the time of the calibration there is no change in the magnitude of the constant voltage applied to the oxygen sensor.

This calibration method is good in accuracy since the concentration of oxygen in the air is constant. However, repeated calibration by this method will adversely affect the durability of the oxygen sensor for the following reason. In a lean-burn engine the nominal air/fuel ratio is usually in the range from about 16 to about 24 by weight, so that the concentration of oxygen in the exhaust gas is in the range from about 1% to about 8%. At the time of calibration the exhaust gas under the atmospheric condition contains about 20% of oxygen. Since the constant voltage applied to the oxygen sensor is invariable the current flowing through the oxygen sensor under calibration becomes 2 to 4 times as large as the current flowing during normal operation for detection of air/fuel ratio. Therefore, deteriorating aging of the solid electrolyte and/or electrodes of the oxygen sensor is significantly accelerated.

SUMMARY OF THE INVENTION

It is an object of the present invention to provide a system for accurately detecting the concentration of oxygen in gases, which includes an oxygen sensor using a solid electrolyte and means for supplying a current to the sensor and in which high accuracy of the oxygen concentration detection is long ensured even though the gas subject to measurement repeatedly becomes equivalent to the atmospheric air.

It is another object of the invention to provide a system for detecting the air/fuel ratio in an internal combustion engine, in which an oxygen concentration detecting system of the invention is used with the oxygen sensor disposed in the exhaust gas passage.

The present invention provides a system for detecting the concentration of oxygen in a gas, which comprises an oxygen sensor comprising gas admitting means for admitting a fraction of a gas subject to inspection, diffusion restricting means for offering a resistance to the inflow of the gas into the gas admitting means, a first solid electrolyte cell which has a layer of an oxygen ion conductive solid electrolyte with its one surface exposed to a preselected gas and the opposite surface exposed to a gas in the gas admitting means and produces an electrical output representing a difference between a partial pressure of oxygen in the preselected gas and a partial pressure of oxygen in the gas in the gas admitting means and a second solid electrolyte cell which has a body of an oxygen ion conductive solid electrolyte and a pair of electrodes arranged such that an externally supplied DC current flows in the solid electrolyte body to cause migration of oxygen ions through the solid electrolyte body and controls the magnitude of the partial pressure of oxygen in a gas in the gas admitting means in dependence on the intensity of the current. The system further comprises current supply means for supplying the aforementioned DC current to the second solid electrolyte cell and controlling the current so as to render the output of the first solid electrolyte cell equal to a predetermined target value, measurement means for detecting the intensity of the current and producing a provisional output signal representing the detected current intensity, atmospheric condition judging means for continually making a judgement whether the gas in the gas admitting means is equivalent to the atmospheric air or not and producing an electrical signal indicating the result of the judgement, shift means for varying the aforementioned target value in response to the signal from the atmospheric condition judging means such that when the signal indicates that the gas in the gas admitting means is equivalent to the atmospheric air the intensity of the aforementioned current becomes lower than the intensity of the same current required if the target value is not varied under the same atmospheric condition, and correction means for correcting the provisional output signal based on the value of the provisional output signal produced when the gas in the gas admitting means is judged equivalent to the atmospheric air and thereby producing an output signal representing the concentration of oxygen in the gas subject to inspection.

In this system calibration of the oxygen sensor is possible by checking the output value while the gas in the gas admitting means of the sensor is equivalent to the air. The primary feature of the invention resides in that the target value which determines the relationship between the oxygen concentration and the required intensity of the current supplied to the oxygen sensor is varied so as to make the required current intensity relatively low when the atmospheric condition is established in the gas admitting means. Therefore, deterioration of the oxygen sensor by the flow of the current therein under the atmospheric conditions is prevented. The lowering of the current intensity for the sensor under the atmospheric condition offers some additional advantages as will be described hereinafter.

The gas subject to inspection itself can be used as the aforementioned preselected gas, though this is not limitative.

A system according to the invention is suitable for use in detecting the air/fuel ratio in an internal combustion engine, which may be an automotive engine, by detecting the concentration of oxygen in the exhaust gas.

BRIEF DESCRIPTION OF THE DRAWINGS

FIG. 4 is a graph showing the output characteristics of a part of the system of FIG. 2;

DESCRIPTION OF THE PREFERRED EMBODIMENTS

Figure 1:
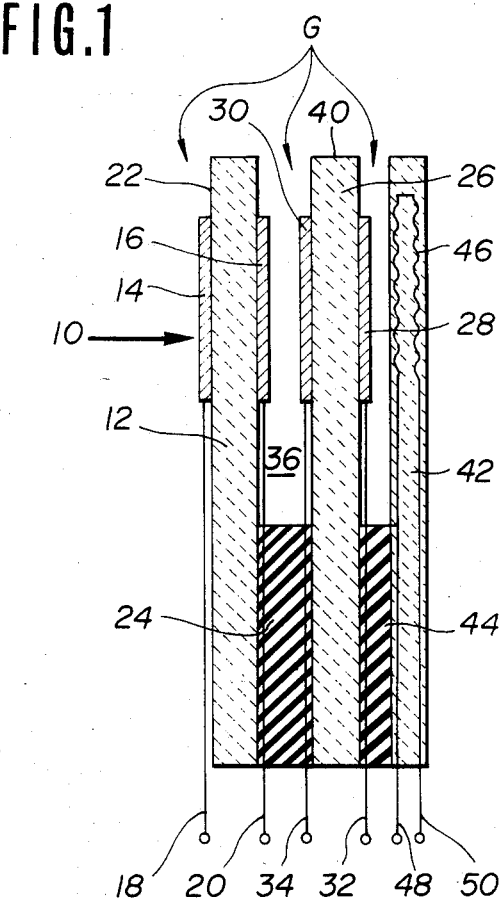
FIG. 1 is a schematic and sectional illustration of an oxygen sensor used in the present invention.

FIG. 1 shows an exemplary construction of the oxygen sensor as a component of a system according to the invention. In the following description the invention is embodied in a system for detecting the air/fuel ratio in an internal combustion engine by detecting the concentration of oxygen in the exhaust gas, and this oxygen sensor 10 is designed so as to be disposed in the exhaust gas passage of the engine.

The oxygen sensor 10 has a flat plate 12 of an oxygen ion conductive solid electrolyte, an anode layer 14 which is formed on an outer surface of the solid electrolyte plate 12 so as to be directly exposed to the exhaust gas and a cathode layer 16 formed on the opposite surface of the plate 12. Leads 18 and 20 extend from the anode 14 and 16, respectively. For example, the solid electrolyte material of the plate 12 is a solid solution of a principal oxide such as $ZrO_2$, $HfO_2$, $ThO_2$ or $Bi_2O_3$ with at least one stabilizing oxide such as $CaO$, $MgO$, $Y_2O_3$ or $YB_2O_3$. The plate 12 is formed by a sintering method. Platinum or gold is preferable as the principal material of the anode 14 and cathode 16. As is well known, the combination of the solid electrolyte plate 12 and the electrodes 14 and 16 serves as an oxygen sensing element of the oxygen concentration cell type. In the following description this combination will be called a sensor cell 22.

The oxygen sensor 10 has another flat plate 26 of an oxygen ion conductive solid electrolyte, which is arranged parallel to the initially described solid electrolyte plate 12 and fixed thereto via a solid and electrochemically inactive spacer 24. An anode layer 28 is formed on an outer surface of the solid electrolyte plate 26 and a cathode layer 30 on the opposite surface which faces the inner surface of the solid electrolyte plate 12 of the sensor cell 22. Leads 32 and 34 extend from the anode 28 and cathode 30, respectively. The same material can be used for the two solid electrolyte plates 12 and 26, and platinum or gold is preferable as the principal material of the electrodes 28 and 30 too. The combination of the second solid electrolyte plate 26 and the electrodes 28 and 30 is similar in construction to the sensor cell 22, but this combination is used for a different purpose. As will be described hereinafter, an externally supplied DC current flows across the solid electrolyte plate 26 from the anode 28 to the cathode 30 to allow oxygen ions to migrate in the solid electrolyte plate 26 from the cathode side toward the anode side. Hereinafter this cell will be called a pump cell 40.

The spacer 24 has an appropriately determined and relatively small thickness such as 0.1 mm. The thickness of the spacer 24 determines the width of a gap 36 between the sensor cell 22 and the pump cell 40. The thicknesses of the sensor cell cathode layer 16 and the pump cell cathode layer 30 are very small and can be neglected in considering the width of the gap 36. The gap 36 provides access to the cathode 16 of the sensor cell 22 and allows a gas G subject to measurement, in this case the exhaust gas, to come into contact with the sensor cell cathode 16 and also with the cathode side of the pump cell 40. However, the narrowness of the gap 36 offers considerable resistance to diffusion of the gas G into this gap 36. Therefore, the gap 36 serves as a gas-admitting and diffusion-restricting means.

To ensure the activity inherent to the solid electrolyte material of the plates 12 and 26, the oxygen sensor 10 includes a heater part. A base plate 42 of a ceramic material such as alumina is fixed to the pump cell 40 via a solid spacer 44, and a heater 46 is embedded in the base plate 42. Numerals 48 and 50 indicate leads of the heater 46. Actually, the spacer 44 has a relatively large thickness so as to allow the gas G to freely come into contact with the anode 28 of the pump cell 40.

Figure 2:
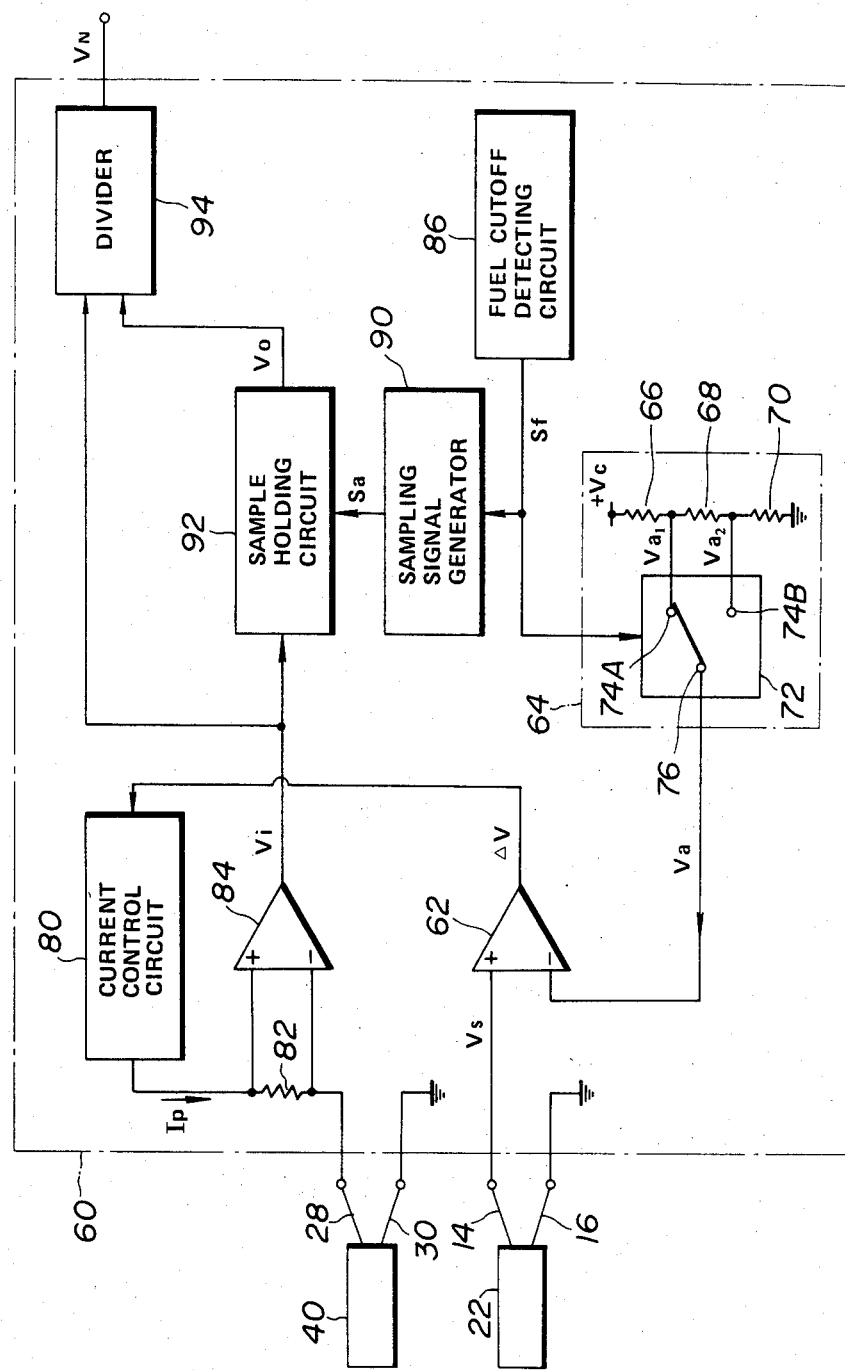
FIG. 2 is a block diagram showing an air/fuel ratio detecting system as an embodiment of the invention.

FIG. 2 shows the construction of a circuit 60 for detecting the air/fuel ratio in the engine by using the above described oxygen sensor 10, which is disposed in the exhaust gas passage. In this example it is assumed that the air/fuel ratio is not lower than the stoichiometric ratio.

The anode 14 of the sensor cell 22 is connected to a differential amplifier 62 to input thereto a voltage $V_s$ at the anode 14 relative to the cathode 16 of the sensor cell 22, and a voltage signal $V_a$ representing a target voltage is supplied to the differential amplifier 62 from a target voltage producing circuit 64. The differential amplifier 62 outputs a voltage signal $\Delta V$ which represents the difference $V_s - V_a$.

There is a current supplying circuit 80 for supplying a DC current $I_p$ to the anode 28 of the pump cell 40 in the oxygen sensor 10. This circuit 80 receives the output $\Delta V$ of the differential amplifier 62 to control the intensity of the current $I_p$ in accordance with the magnitude of the voltage $\Delta V$ with the aim of nullifying the differential voltage $\Delta V$ by the function of the pump cell 40. That is, the aim is: $\Delta V=0$, hence $V_s=V_a$. Thus, the differential amplifier 62 and the current supplying circuit 80 constitute a controlled current supplying means.

A resistor 82 is interposed between the current supplying circuit 80 and the pump cell anode 28, and a differential amplifier 84 provides a voltage signal $V_i$ which represents a voltage across the resistor 82 and, therefore, the intensity of the current $I_p$.

The aforementioned target voltage producing circuit 64 has resistors 66, 68 and 70 to produce a first target voltage $V_{a1}$ and a second target voltage $V_{a2}$ ($V_{a1} > V_{a2}$) by dividing a constant voltage $+V_c$, and this circuit 64 includes a voltage-responsive switch 72 having two input terminals 74A and 74B to which the first and second target voltages $V_{a1}$ and $V_{a2}$ are applied, respectively, and an output terminal 76 which is connected with the differential amplifier 62. The switch 72 is governed by the output of a fuel-cut detecting circuit 86. This circuit 86 makes a judgement whether the feed of fuel to the engine is continuing or cut off by using suitable input signals such as engine speed signal, vehicle speed signal and throttle position signal and outputs a two-level voltage signal $S_f$ which becomes "L" (low level) signal when cut-off of fuel is recognized and otherwise remains as "H" (high level) signal. In the switch 72, the output terminal 76 is connected to the first input terminal 74A to choose the first target voltage $V_{a1}$ when the output $S_f$ of the fuel-cut detecting circuit 86 is "H" signal, and to the other input terminal 74B to choose the second target voltage $V_{a2}$ when the signal $S_f$ is "L" signal.

The output $S_f$ of the fuel-cut detecting circuit 86 is supplied to a sampling signal generator 90 too. This signal generator 90 outputs a two-level voltage signal $S_a$ which is "L" signal while the supplied signal $S_f$ is "H" signal and turns into "H" signal after the lapse of a predetermined length of time, $\Delta t$, from a change of the fuel-cut signal $S_f$ from "H" to "L". The reason for the provision of this signal generator 90 is that even though fuel is cut off the exhaust gas does not immediately become equivalent to the atmosphere. Thus, the combination of the fuel-cut detecting circuit 86 and the sampling signal generator-90 constitute an atmospheric condition determination means.

The sampling signal $S_a$ is supplied to a sample holding circuit 92, which continuously receives the output $V_i$ of the differential amplifier 84 and, when the sampling signal $S_a$ turns into "H", holds the signal $V_i$ at that moment and outputs an equivalent voltage signal $V_0$ which will be called a reference voltage.

An output part of the air/fuel ratio detecting circuit 60 is a divider 94 to which the reference voltage $V_0$ and the output $V_i$ of the differential amplifier 84 are input. The divider 94 outputs an air/fuel ratio signal $V_N$, which is a variable voltage signal representing the result of dividing $V_i$ by $V_0$, i.e. $V_N = V_i/V_0$. Thus, the sampling signal generator 90, sample holding circuit 92 and divider 94 constitute an output correcting means.

The following is a description of the operation of the air/fuel ratio detecting system comprising the oxygen sensor 10 of FIG. 1 and the circuit 60 of FIG. 2.

In the oxygen sensor 10, the anode 14 of the sensor cell 22 is exposed to the exhaust gas G produced by combustion of a fuel-lean air-fuel mixture. The exhaust gas G has an oxygen partial pressure $P_x$. A very small portion of the exhaust gas G enters the narrow gap 36 between the sensor cell 22 and the pump cell 40, while the current $I_p$ flows in the pump cell 40 so as to force oxygen ions to migrate through the solid electrolyte plate 26 from its cathode side toward the outer anode side. Therefore, an oxygen partial pressure $P_y$ in this gap 36 is lower than $P_x$. Accordingly the sensor cell 22 generates a voltage $V_s$ between its anode 14 and cathode 16, and this voltage $V_s$ is determined by the Nernst equation:

$$V_s = (RT/4F)\log_e(P_x/P_y)$$

where R is the gas constant, F is the Faraday constant, and T represents absolute temperature.

As mentioned hereinbefore, the intensity of the current $I_p$ is controlled so as to keep the sensor output voltage $V_s$ constant and equal to the target voltage $V_a$. In other words, the current $I_p$ is controlled so as to keep the oxygen partial pressure ratio $P_x/P_y$ constant by varying the oxygen partial pressure $P_y$ in the gap 36. Representing the diffusion coefficient of the gap 36 by D, the amount of oxygen Q admitted into the gap 36 is given by:

$$Q = D(P_x - P_y)$$

Since the pump current $I_p$ is controlled so as to keep $P_x/P_y$ constant, $I_p$ becomes proportional to Q. Therefore, $$I_p = K(P_x - P_y)$$

where K is a constant.

Figure 3:
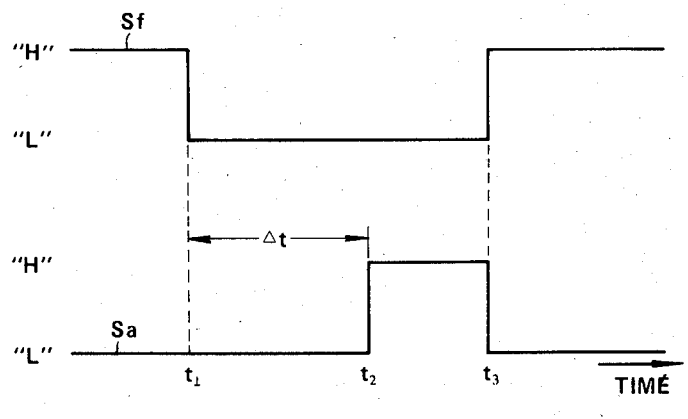
FIG. 3 is a timing chart for explanation of the function of a part of the system of FIG. 2.

The chart of FIG. 3 illustrates the function of the sampling signal generator 90. While the fuel-cut detecting circuit 86 is assuming that fuel is not cut off, viz. before timepoint $t_1$, the fuel signal $S_f$ remains in the "H" state, so that the target voltage producing circuit 64 selects the first target voltage $V_{a1}$ as its output $V_a$. Therefore, the relationship between the oxygen partial pressure $P_x$ in the exhaust gas G and the pump current $I_p$ or voltage $V_i$ as the output of the differential amplifier 84 is determined by the first target voltage $V_{a1}$. When the fuel-cut detecting circuit 86 makes a determination that the fuel is cut off at timepoint $t_1$ the fuel signal $S_f$ immediately shifts to the "L" state. In response, the target voltage producing circuit 64 changes the magnitude of its output $V_a$ to the relatively low second target voltage $V_{a2}$, so that a change occurs in the relationship between the oxygen partial pressure $P_x$ and the output $V_i$ of the differential amplifier 84. After the lapse of the predetermined length of time $\Delta t$ from $t_1$, viz. at timepoint $t_2$, the sampling signal generator 90 shifts its output $S_a$ from "L" state to "H" state to thereby command the sample holding circuit 92 to hold the voltage $V_i$ at that moment and to output the same voltage as the reference voltage $V_0$. That is, the reference voltage $V_0$ represents the value of the voltage $V_i$ produced while the exhaust gas G is equivalent to the atmosphere. At timepoint $t_3$ the fuel-cut detecting circuit 86 detects that the feed of fuel is resumed and shifts its output $S_f$ from "L" state to "H" state. In response, the target voltage producing circuit 64 restores the value of its output $V_a$ to the relatively high first target voltage $V_{a1}$, and the sampling signal generator 90 shifts its output $S_a$ from "H" state to "L" state. At this timepoint $t_3$ a change occurs in the relationship between the oxygen partial pressure $P_x$ and the produced voltage $V_i$, but the reference voltage $V_0$ as the output of the sample holding circuit 92 remains unchanged.

Irrespective of the values of the target voltage $V_a$ supplied to the differential amplifier 62, the divider 94 continues to divide the voltage $V_i$, which may be called an uncorrected air/fuel ratio signal, by the reference voltage $V_0$ to thereby output the corrected air/fuel ratio signal $V_N$.

Referring to FIG. 4, when the first target voltage $V_{a1}$ is chosen as the output $V_a$ of the target voltage producing circuit 64, the relationship between the content of oxygen in the exhaust gas and the uncorrected air/fuel ratio signal $V_i$ produced by using an oxygen sensor A of the construction shown in FIG. 1 will become as represented by the curve A, and the same relationship will become as represented by the curve B when another oxygen sensor B of the same construction and slightly different characteristics is used. Alternatively, the curve B may be taken as represents the result of some deterioration of the oxygen sensor A during its long use. When the second target voltage $V_{a2}$, which is lower than $V_{a1}$, is used the relationship between the oxygen content in the exhaust gas and the uncorrected air/fuel ratio signal $V_i$ will become as represented by the curve A' with respect to the oxygen sensor A, and as represented by the curve B' with respect to the oxygen sensor B.

Figure 5:
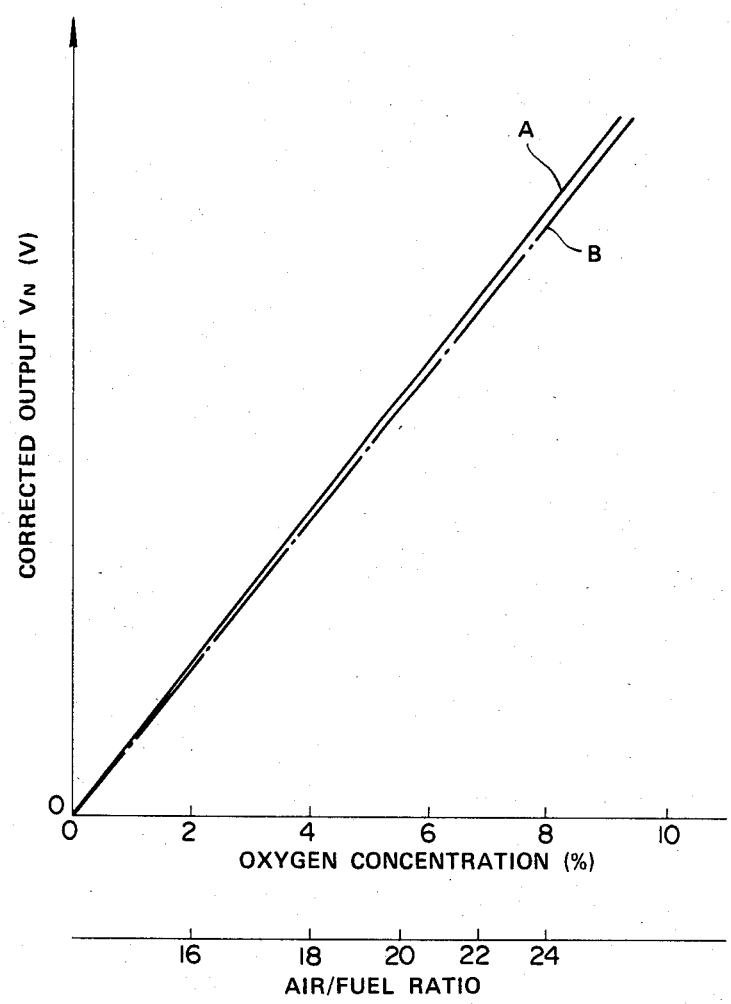
FIG. 5 is a graph showing the final output characteristics of the system of FIG. 2.

In FIG. 4, when the higher target voltage $V_{a1}$ is used and the exhaust gas is equivalent to the atmosphere, the uncorrected air/fuel ratio signal $V_i$ becomes $V_{A1}$ volt with respect to the oxygen sensor A and $V_{B1}$ volt with respect to the oxygen sensor B. When the lower target voltage $V_{a2}$ is used under the same atmospheric condition, $V_i$ becomes $V_{A2}$ volt with respect to the sensor A and $V_{B2}$ volt with respect to the sensor B. The difference in oxygen-sensing characteristics between the two oxygen sensors A and B can be represented by the voltage ratio $V_{A1}/V_{B1}$ and also by the other voltage ratio $V_{A2}/V_{B2}$. As can be seen in FIG. 4, the ratio $V_{A2}/V_{B2}$ is approximately equal to the ratio $V_{A1}/V_{B1}$. In the so-called leanburn engines a normally employed range of the air/fuel ratio is from about 15 to about 24 by weight, so that the concentration of oxygen in the exhaust gas ranges from about 0% to about 8%. In the air/fuel ratio detecting circuit 60 of FIG. 2 the first target voltage $V_{a1}$ is used while the air/fuel ratio is in the normally employed range, and the corrected air/fuel ratio signal $V_N$ is produced by dividing the intermediately produced signal $V_i$ by the reference voltage $V_0$ produced when the exhaust gas is equivalent to the atmosphere and the second target voltage $V_{a2}$ is used. That is, the corrected air/fuel ratio signal $V_N$ is equal to $V_i/V_{A2}$ with respect to the oxygen sensor A and to $V_i/V_{B2}$ with respect to the oxygen sensor B. Consequently, the oxygen sensors A and B which are somewhat different in oxygen-sensitive characteristics provide approximately the same air/fuel ratio signal $V_N$ as represented by the curves A and B in FIG. 5.

In the practice of the present invention, some differences in oxygen-sensitive characteristics among mass-produced oxygen sensors of the same design or some changes in the characteristics of the individual oxygen sensors by aging do not lead to significant changes in the relationship between the oxygen concentration in the exhaust gas and the corrected air/fuel signal $V_N$. Each oxygen sensor used in a system according to the invention can be calibrated by examining the magnitude of the uncorrected air/fuel ratio signal $V_i$ while the exhaust gas is equivalent to the atmosphere and the second target voltage $V_{a2}$ is used. As will be understood from FIG. 4, the intensity of the current $I_p$ supplied to the pump cell 40 of the oxygen sensor during the calibration becomes less than a half of the current intensity in the case of using the higher target voltage $V_{a1}$ even when calibrating the oxygen sensor under the atmospheric condition. In the present invention, the intensity of the pump current $I_p$ for the calibration is very close to the maximal value of the pump current $I_p$ during normal detection operation. This means that the possibility of deterioration of the solid electrolyte 26 and electrodes 28, 30 of the pump cell 40 by the flow of an excessively large current therethrough is obviated, and accordingly this leads to improved service life of the oxygen sensor. Furthermore, the great decrease in the maximum value of the pump current $I_p$ contributes to enhancement of the accuracy of the intermediately produced signal $V_i$. Besides, the decrease in the maximum value of the pump current $I_p$ (under the atmospheric condition) allows to reduce the functional capacity of the current supplying circuit 80. For example, it becomes possible to use current-controlling transistors of relatively small capacity. This leads to a reduction in the production cost.

In the above described embodiment the gas subject to measurement, i.e. exhaust gas, itself is used as a reference gas. However, this is not limitative. For example, the oxygen sensor may be modified so as to use the atmospheric air as a reference gas. In the oxygen sensor 10 of FIG. 1 the narrow gap 36 is employed as a gas diffusion-restricting means, but this is not limitative either. For example, a small hole that defines an inlet opening to a gas-admitting chamber or a porous body fitted in an inlet opening of a gas-admitting chamber may alternatively be employed as the diffusion-restricting means. Furthermore, the above described air/fuel ratio detecting system can be modified so as to perform the detection over a wider range of air/fuel ratio including air/fuel ratios below the stoichiometric ratio. As will be understood, the polarity of the pump current $I_p$ is reversed when detecting air/fuel ratios below the stoichiometric.

Figure 6:
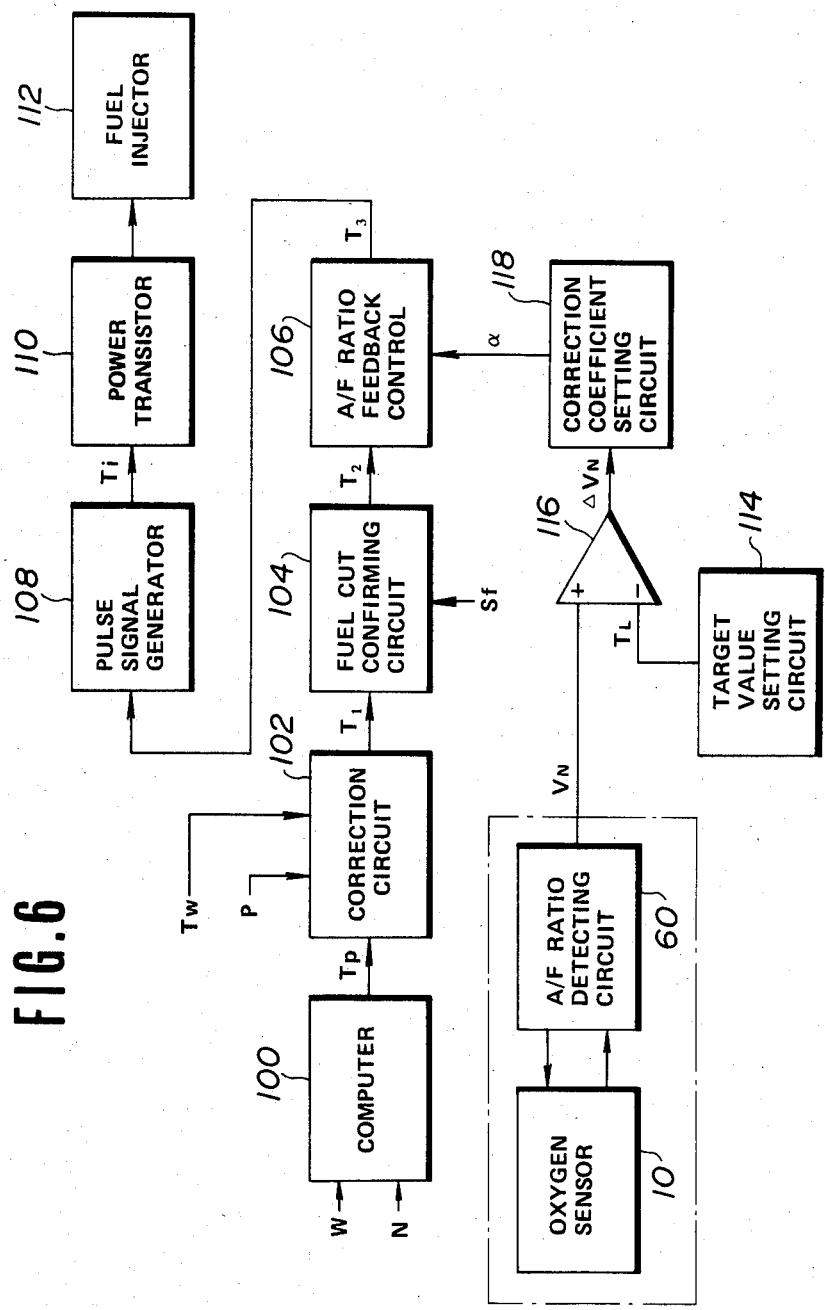
FIG. 6 is a block diagram showing a fuel injection control system in which the air/fuel ratio detecting system of FIG. 2 is incorporated.

FIG. 6 illustrates the application of the above described air/fuel ratio detection system to an electronically controlled fuel injection system in an automotive engine.

A computer 100 computes a standard amount of fuel injection per revolution of the engine based on the flow rate of air W taken into the engine and rpm of the engine N. In a correction circuit 102 the output $T_p$ of the computer 100 is corrected based on various factors including the cooling water temperature $T_w$ and the throttle valve position P to provide a signal $T_1$ representing a first corrected amount of fuel injection. The signal $T_1$ is passed to a fuel-cut confirming circuit 104, which receives the fuel signal $S_f$ from the fuel-cut detecting circuit 86 in FIG. 2 and converts the signal $T_1$ into another signal $T_2$ which is identical with the original signal $T_1$ when the fuel signal $S_f$ is in "H" state and becomes null when the signal $S_f$ is in "L" state indicating the cutoff of fuel. This output $T_2$ is passed to an air/fuel ratio feedback circuit 106 to which the air/fuel ratio detection circuit 60 of FIG. 2 is connected in the following manner.

The system of FIG. 6 includes a signal generator 114 which generates a signal $T_L$ representing an intended air/fuel ratio. The corrected air/fuel ratio signal $V_N$ produced by the circuit 60 of FIG. 2 and the aimed air/fuel ratio signal $V_L$ are input to a differential amplifier 116, which outputs a voltage signal $\Delta V_N$ representing a difference between $V_N$ and $V_L$: $\Delta V_N = V_N - V_L$. In a correction coefficient setting circuit 118, the signal $\Delta V_N$ is subjected to an integration treatment using a predetermined integration coefficient. The output $\alpha$ of the circuit 118 represents an air/fuel ratio correction coefficient. In the air/fuel ratio feedback circuit 106, the signal $T_2$ representing the amount of fuel injection is multiplied by the coefficient $\alpha$ to provide another signal $T_3$ which represents an appropriate amount of fuel injection to correct a deviation of the actual air/fuel ratio from the intended air/fuel ratio.

Based on the output $T_3$ of the air/fuel ratio feedback circuit 106, a pulse signal generator 108 produces a pulse signal $T_i$ the duration of which corresponds to the amount of fuel injection indicated by the signal $T_3$. The signal generator 108 may include a circuit for correcting the signal $T_3$ according to the actual value of the onboard battery voltage in advance of producing the pulse signal $T_i$. This pulse signal $T_i$ is supplied to a power transistor 110, or an alternative device, for actuating each fuel injection valve 112. In this system the air/fuel ratio can be controlled very accurately since the air/fuel ratio signal $V_N$ produced by the circuit 60 of FIG. 2 accurately represents the oxygen concentration in the exhaust gas, and accordingly an actual air/fuel ratio in the engine, at every moment without being significantly affected by aging deterioration of the oxygen sensor 10 or by differences among the individuals of industrially produced oxygen sensors in their oxygen-sensitive characteristics. In this case, the air/fuel ratio signal correcting means 90, 92, 94 in FIG. 2 may be transferred into the fuel injection control system of FIG. 6, if desired.

In the foregoing description a system according to the invention is used in detecting the concentration of oxygen in the exhaust gas of an automotive internal combustion engine, but this is not limitative. This invention is applicable to various kinds of combustors including stationary engines in plants, blast furnaces and internal combustion engines on ships for detecting either the concentration of oxygen in the exhaust or combustion gases or the air/fuel ratio in the combustors. Accordingly, the method of detecting the change of the gas subject to measurement into the atmospheric condition is not limited to the detection of cutoff of fuel feed as in the above described embodiment.

What is claimed is:

1. A system for detecting the concentration of oxygen in a gas, comprising:

an oxygen sensor comprising gas admitting means for admitting a fraction of a gas subject to inspection, diffusion restricting means for offering a resistance to the inflow of said gas into said gas admitting means, a first solid electrolyte cell which comprises a layer of an oxygen ion conductive solid electrolyte with its one surface exposed to a preselected gas and the opposite surface exposed to a gas in said gas admitting means and produces an electrical output representing a difference between a partial pressure of oxygen of said preselected gas and a partial pressure of oxygen of the gas in said gas admitting means, and a second solid electrolyte cell which comprises a body of an oxygen ion conductive solid electrolyte and a pair of electrodes arranged such that an externally supplied DC current flows in the solid electrolyte body to cause migration of oxygen ions through the solid electrolyte body and controls the magnitude of the partial pressure of oxygen in a gas in said gas admitting means in dependence on the intensity of said current;

current supply means for supplying said DC current to said second solid electrolyte cell and controlling said current so as to render said output of said first solid electrolyte cell equal to a predetermined target value;

measurement means for detecting the intensity of said current and producing a provisional output signal representing the detected current intensity;

atmospheric condition determining means for continually making a determination whether the gas in said admitting means is equivalent to the atmospheric air or not and producing an electrical signal indicating the result of the determination;

shift means for varying said target value in response to said signal produced by said determining means such that when said signal produced by said determining means indicates that the gas in said gas admitting means is equivalent to the atmospheric air the intensity of said current becomes lower than the intensity of the same current required if the target value is not varied under the same atmospheric condition; and correction means for correcting said provisional output signal based on the value of said provisional output signal produced when the gas in said gas admitting means is determined equivalent to the atmospheric air and thereby producing an output signal representing the concentration of oxygen in the gas subject to inspection.

2. A system according to claim 1, wherein said gas admitting means comprises a space defined between said first and second solid electrolyte cells.

3. A system according to claim 2, wherein said diffusion restricting means comprises a narrow inlet opening which communicates with said space.

4. A system according to claim 3, wherein the solid electrolyte layer of said first solid electrolyte cell is in the form of a substantially flat plate and the solid electrolyte body of said second solid electrolyte cell is in the form of a substantially flat plate which is held opposite to the solid electrolyte plate of said first solid electrolyte cell so as to provide a narrow gap therebetween, said narrow gap being used as said space and an end portion of said gap being used as said inlet opening.

5. A system according to claim 4, wherein one of said electrodes of said second solid electrolyte cell is formed on the surface of the solid electrolyte plate which faces said gap and the other is formed on the opposite surface of the solid electrolyte plate.

6. A system according to claim 1, wherein said preselected gas is the gas subject to inspection.

7. A system according to claim 1, wherein said current supply means comprises means for producing a deviation signal representing a difference between said output of said first solid electrolyte cell and said target value and means for controlling said current in response to said deviation signal.

8. A system according to claim 1, wherein said measurement means comprises a resistor through which said current flows to said second solid electrolyte cell and means for producing a voltage signal representing a voltage across said resistor as said provisional output signal.

9. A system according to claim 8, wherein said shift means comprises switching means which is responsive to said signal produced by said atmospheric condition determining means and normally selects a first voltage as said target value but selects a second lower voltage as said target value when said signal produced by said determining means indicates that the gas in said gas admitting means is equivalent to the atmospheric air.

10. A system according to claim 9, wherein said correction means comprises means for dividing said provisional output signal produced at any moment by a voltage signal which is obtained by holding said provisional output signal while the gas in said gas admitting means is equivalent to the atmospheric air to utilize the result of the division as said output signal.

11. A system for detecting the air/fuel ratio in an internal combustion engine, comprising:
   an oxygen sensor comprising gas admitting means for admitting a fraction of the exhaust gas of the engine, diffusion restricting means for offering a resistance of the inflow of the exhaust gas into said gas admitting means, a first solid electrolyte cell which comprises a layer of an oxygen ion conductive solid electrolyte with its outer one surface exposed to the exhaust gas and the opposite surface exposed to the exhaust gas admitted into said gas admitting means and produces an electrical output representing a difference between a partial pressure of oxygen in the exhaust gas to which said outer one surface is exposed and a partial pressure of the gas in said gas admitting means, and a second solid electrolyte cell which comprises a body of an oxygen ion conductive solid electrolyte and a pair of electrodes arranged such that an externally supplied DC current flows in the solid electrolyte body to cause migration of oxygen ions through the solid electrolyte body and controls the magnitude of the partial pressure of oxygen in the gas in said gas admitting means in dependence on the intensity of said current;
   current supply means for supplying said DC current to said second solid electrolyte cell and controlling said current so as to render said output of said first solid electrolyte cell equal to a predetermined target value;
   measurement means for detecting the intensity of said current and producing a provisional output signal representing the detected current intensity;
   atmospheric condition determining means for continually making a determination whether the gas in said gas admitting means is equivalent to the atmospheric air or not and producing an electrical signal indicating the result of the determination;
   shift means for varying said target value in response to said signal produced by said determining means such that when said signal produced by said determining means indicates that the gas in said gas admitting means is equivalent to the atmospheric air the intensity of said current becomes lower than the intensity of the same current required if said target value is not varied under the same atmospheric condition; and
   correction means for correcting said provisional output signal based on the value of said provisional output signal produced when the gas in said gas admitting means is equivalent to the atmospheric air and thereby producing an output signal representing the concentration of oxygen in the exhaust gas and accordingly representing the air/fuel ratio in the engine.

12. A system according to claim 11, wherein the solid electrolyte layer of said first solid electrolyte cell is in the form of a substantially flat plate and the solid electrolyte body of said second solid electrolyte cell is in the form of a substantially flat plate which is held opposite to the solid electrolyte plate of said first solid electrolyte cell so as to provide a narrow space therebetween, said narrow space being used as said gas admitting means and an end portion of said narrow space being used as said diffusion restricting means.

13. A system according to claim 12, wherein said first solid electrolyte cell further comprises two electrode layers formed on the two opposite major surfaces of the solid electrolyte plate, respectively, and wherein a first one of said electrodes of said second solid electrolyte cell being formed on the surface of the solid electrolyte plate which faces said space and a second one being formed on the opposite surfaces of the solid electrolyte plate.

14. A system according to claim 13, wherein said current flows in said second solid electrolyte cell from said second electrode to said first electrode.

15. A system according to claim 13, wherein said current supply means comprises means for producing a deviation signal representing a difference between said output of said first solid electrolyte cell and said target value and means for controlling said current in response to said deviation signal.

16. A system according to claim 15, wherein said measurement means comprises a resistor through which said current flows to said second solid electrolyte cell and means for producing a voltage signal representing a voltage across said resistor as said provisional output signal.

17. A system according to claim 16, wherein said shift means comprises switching means which is responsive to said signal produced by said determining means and normally selects a first voltage as said target value but selects a second lower voltage as said target value when said signal produced by said determining means indicates that the gas in said gas admitting means is equivalent to the atmospheric air.

18. A system according to claim 17, wherein said atmospheric condition determining means comprises means for detecting cutoff of fuel feed to the engine.

19. A system according to claim 18, wherein said correction means comprises means for dividing said provisional output signal produced at any moment by a voltage signal which is obtained by holding said provisional output signal after the lapse of a predetermined length of time from the moment of detection of cutoff of fuel feed by said determining means to utilize the result of the division as said output signal.

* * * * *